(12) United States Patent
Robl

(10) Patent No.: US 6,509,330 B2
(45) Date of Patent: Jan. 21, 2003

(54) HYDROXAMIC ACID CONTAINING COMPOUNDS USEFUL AS ACE INHIBITORS AND/OR NEP INHIBOTORS

(75) Inventor: Jeffrey A. Robl, Newtown, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 09/780,747

(22) Filed: Feb. 9, 2001

(65) Prior Publication Data

US 2002/0193562 A1 Dec. 19, 2002

Related U.S. Application Data

(60) Provisional application No. 60/183,259, filed on Feb. 17, 2000.

(51) Int. Cl.[7] .................. A61K 31/55; C07D 487/00; C07D 498/00; C07D 223/12; A61P 9/12
(52) U.S. Cl. .............. 514/212.02; 514/212.03; 514/212.08; 540/523; 540/527
(58) Field of Search ................. 540/527, 524, 540/523; 514/212.03, 212.08, 212.02

(56) References Cited

U.S. PATENT DOCUMENTS

| | | | | |
|---|---|---|---|---|
| 4,996,358 A | | 2/1991 | Handa et al. | ................ 562/621 |
| 5,672,598 A | * | 9/1997 | De et al. | .................... 514/212 |

FOREIGN PATENT DOCUMENTS

| | | |
|---|---|---|
| EP | 0236872 A2 | 9/1987 |
| EP | 0534363 A2 | 9/1992 |
| EP | 0524553 A1 | 1/1993 |
| EP | 0599444 A1 | 5/1993 |
| EP | 0629627 A2 | 6/1994 |
| EP | 0655461 A1 | 5/1995 |
| EP | WO 97/38705 | 10/1997 |

OTHER PUBLICATIONS

Natchus et al. (Bioorg. Med. Chem. Lett. (1988), 8(16), 2077–2080.*

Nishino et al, "*Pseudomonas aeruginosa* Elastase Development of a new substrate, Inhibitors, and an Affinity Ligant", The Journal of Biological Chemistry, vol. 255, No. 8, Apr. 25, pp. 3482–3486, 1980.

Nishino et al, Design of Potent Reversible Inhibitors for Thermolysin. Peotides Containing Zinc Coordinating Ligands and Their Use in Affinity Chromatography: American Chemical Society, vol. 18, No. 20, pp. 4340–4347, 1979.

Weller et al, "Design of Conformationally Constrained Angiotensin–Converting Enzyme Inhibitors" Biochemical and Biophysical Research Communications, vol. 125, No. 1, pp. 82–89, Nov. 30, 1984.

Weller et al. Biochemical & Biophysical Research Communication. vol. 125. No. 1, (1984) pp. 82–89.

Fournie–Zaluski. et al. Journal of Medicinal Chemistry, vol. 28, N. 9, (1985) pp. 1158–1169.

Nishino et al. Biochemistry, vol. 18, No. 20, (1979), pp. 4340–4347.

* cited by examiner

*Primary Examiner*—Bruck Kifle
(74) *Attorney, Agent, or Firm*—Burton Rodney

(57) ABSTRACT

Hydroxamic acids are provided which are ACE and/or NEP inhibitors and have the structure

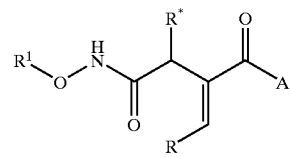

wherein R*, R and R[1] are as defined herein and A is a dipeptide preferably derived from an amino acid, or is a conformationally restricted dipeptide mimic.

4 Claims, No Drawings

HYDROXAMIC ACID CONTAINING COMPOUNDS USEFUL AS ACE INHIBITORS AND/OR NEP INHIBOTORS

This application claims priority from U.S. Provisional Application Ser. No. 60/183,259, filed Feb. 17, 2000.

SUMMARY OF THE INVENTION

This invention is directed to novel compounds possessing angiotensin converting enzyme (ACE) inhibitory activity and/or neutral endopeptidase (NEP) inhibitory activity and methods of preparing such compounds. This invention is also directed to pharmaceutical compositions containing such ACE and/or NEP inhibiting compounds or pharmaceutically acceptable salts thereof and the method of using such compositions.

The compounds of this invention are those of the formula (I)

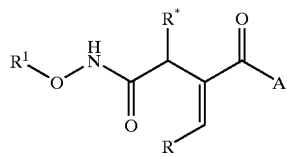

including a pharmaceutically acceptable salt thereof where:

in the moiety

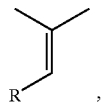

"‖" denotes a single bond or a double bond, and the R group may be in the cis or trans configuration;

R and R* are the same or different and are independently selected from H, alkyl, alkenyl, aryl-$(CH_2)_p$—, heteroaryl-$(CH_2)_p$—, or cycloheteroalkyl-$(CH_2)_p$—; $R^1$ is H or —$COR^2$ where $R^2$ is alkyl, aryl-$(CH_2)_p$—, cycloheteroalkyl-$(CH_2)_p$—, heteroaryl-$(CH_2)_p$—, alkoxy, or cycloalkyl-$(CH_2)_p$—;

p is 0 or an integer from 1 to 8; and

A is a dipeptide, preferably derived from one or two non-proteinogenic amino acids or is a conformationally restricted dipeptide mimic as described below.

A can be a dipeptide derivative of the structure

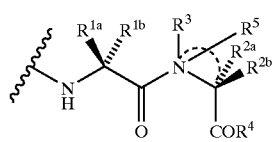

A(1)

where $R^{1a}$, $R^{1b}$, $R^{2a}$ and $R^{2b}$ are independently selected from H, alkyl, aryl-$(CH_2)_p$—, cycloalkyl, cycloheteroalkyl-$(CH_2)_p$—, heteroaryl-$(CH_2)_p$—, biphenylmethyl, or $R^{1a}$ and $R^{1b}$ or $R^{2a}$ and $R^{2b}$ may be joined together to the carbon to which they are attached to form a 3 to 7 membered ring, optionally fused to a benzene ring; and

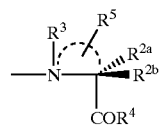

refers to an optional 5 or 6 membered ring containing a single hetero atom and which may optionally include an $R^5$ substituent (as shown) which is H, alkyl, aryl-$(CH_2)_p$, cycloalkyl-$(CH_2)_p$, cycloheteroalkyl-$(CH_2)_p$, or cycloheteroaryl-$(CH_2)_p$—;

$R^3$ is H, alkyl or aryl -$(CH_2)_p$—;

$R^4$ is OH, Oalkyl, or —O—$(CH_2)_p$aryl.

In addition, A can be a conformationally restricted dipeptide mimic which has the structure

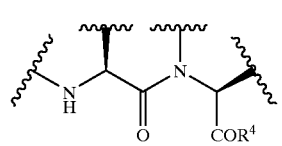

A(2)

and is a non-proteinogenic dipeptide.

Thus, the compounds of formula I include

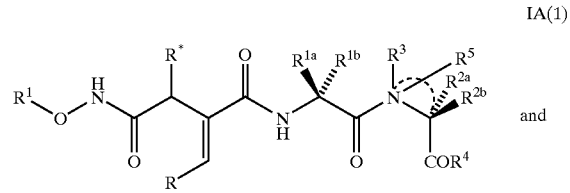

IA(1)

and

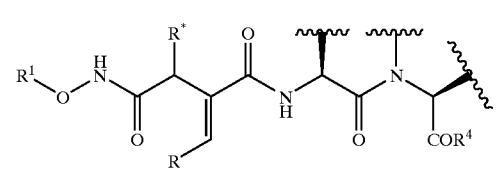

IA(2)

The term "conformationally restricted dipeptide mimic" refers to a structural skeleton which has the attributes of a conventional dipeptide

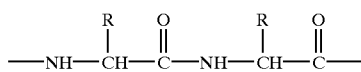

but having enhanced biological properties due to additional bonds which limit the rotational freedom.

Examples of the A(2) dipeptide mimics include any of the conformationally restricted dipeptide mimics set out below.

A(3)
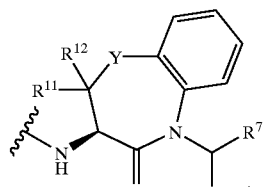
where Y = O, S, CH$_2$
or S(O)$_{0,1,2}$
A(4)
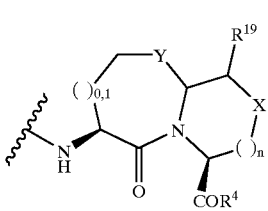
n = 0 or 1
where X = CH$_2$ and
Y = O, S, CH$_2$ or S(O)$_{0,1,2}$
and X = O, S when n = 1
A(5)
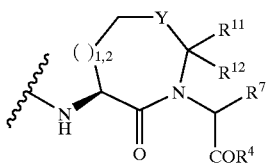
where Y = O, S, CH$_2$
or S(O)$_{0,1,2}$
A(6)
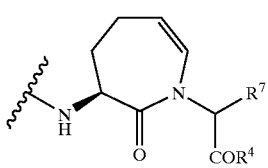
A(7)
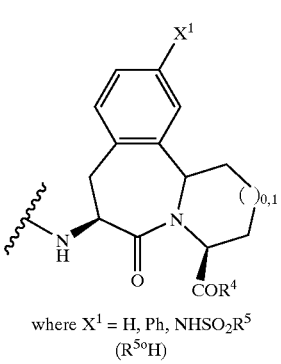
where X$^1$ = H, Ph, NHSO$_2$R$^5$
(R$^{5o}$H)
-continued
A(8)
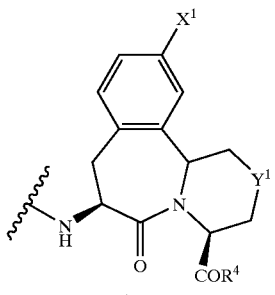
where Y$^1$ = O, S, NH
or S(O)$_n$,
where X$^1$ = H, Ph, NHSO$_2$R$^5$
(R$^{5o}$H)
A(9)
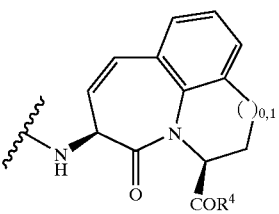
A(10)
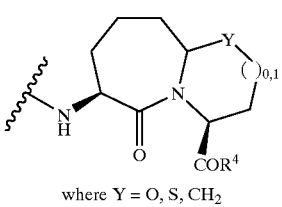
where Y = O, S, CH$_2$
or S(O)$_{0,1,2}$
A(11)
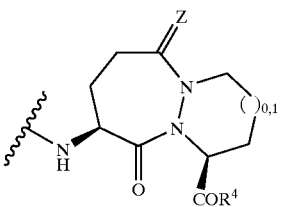
where Z = O or H, H
A(12)
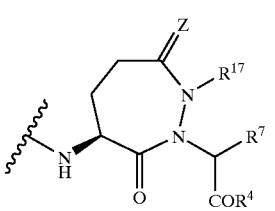
where Z = O or H, H
A(13)
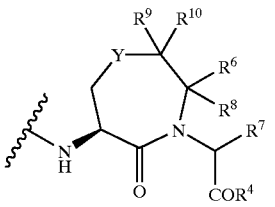
where Y = O, S, CH$_2$
or S(O)$_{0,1,2}$ A(14)
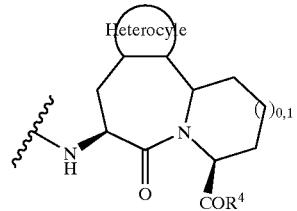

A(15)
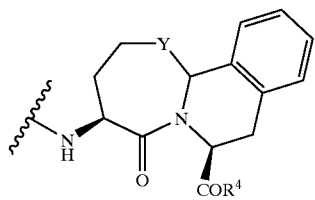

where Y = O, S, or S(O)$_{0,1,2}$

A(16)
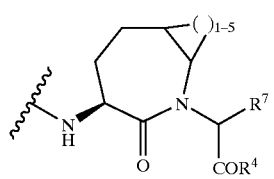

A(17)
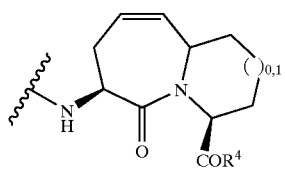

A(18)
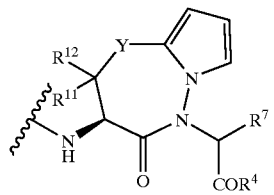

where Y = O, S, CH$_2$

A(19)
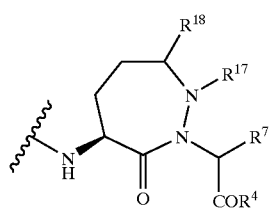

A(20)
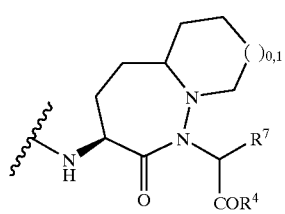

A(21)
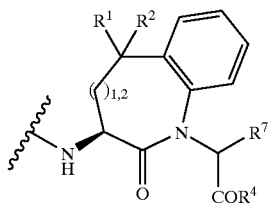

A(22)
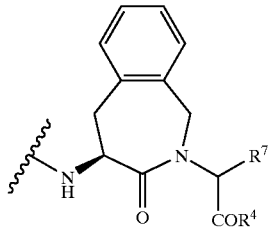

A(23)
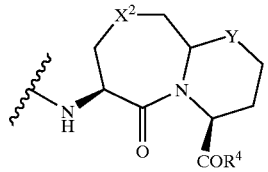

where Y = O, S, CH$_2$ or S(O)$_{0,1,2}$
X$^2$ = O, S(O)$_{0,1,2}$, CH$_2$

A(24)
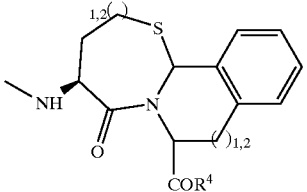

A(25)
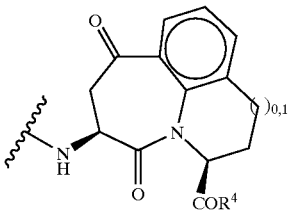

With respect to A(5), $R^{11}$ and $R^{12}$ are independently selected from hydrogen, alkyl, substituted alkyl, alkenyl, substituted alkenyl, cycloalkyl-(CH$_2$)$_m$—, aryl-(CH$_2$)$_m$—, substituted aryl-(CH$_2$)$_m$—, and heteroaryl-(CH$_2$)$_m$—, or $R^{11}$ and $R^{12}$ taken together with the carbon to which they are attached complete a saturated cycloalkyl ring of 3 to 7 carbons, or $R^{11}$ and $R^{12}$ taken together with the carbon to which they are attached complete a keto substituent, i.e.,

with respect to A(13) $R^8$, $R^9$ and $R^7$ are independently selected from hydrogen, alkyl, substituted alkyl, alkenyl, substituted alkenyl, cycloalkyl-$(CH_2)_m$—, aryl-$(CH_2)_m$—, substituted aryl-$(CH_2)_m$—, and heteroaryl-$(CH_2)_m$—;

$R^{10}$ and $R^6$ are independently selected from hydrogen, alkyl, substituted alkyl, alkenyl, substituted alkenyl, cycloalkyl-$(CH_2)_m$—, aryl-$(CH_2)_m$, substituted aryl-$(CH_2)_m$—, and heteroaryl-$(CH_2)_m$—, or $R^6$ and $R^{10}$ taken together with the carbon to which they are attached complete a saturated cycloalkyl ring of 3 to 7 carbons, $R^6$ and $R^8$ taken together with the carbon to which they are attached complete a saturated cycloalkyl ring of 3 to 7 carbons, or $R^9$ and $R^{10}$ taken together with the carbon to which they are attached complete a saturated cycloalkyl ring of 3 to 7 carbons;

m is zero or an integer from 1 to 6;

$R^4$ is OH, Oalkyl, O—$(CH_2)_m$-heteroaryl,

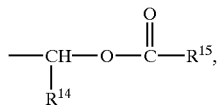

O—$(CH_2)_m$-aryl, or

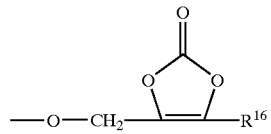

or $NR_1(R_2)$;

where $R_1$ and $R_2$ are independently H, alkyl, aryl$(CH_2)_p$, aryl or heteroaryl;

$R^{14}$ is hydrogen, lower alkyl, cycloalkyl, or phenyl;

$R^{15}$ is hydrogen, lower alkyl, lower alkoxy or phenyl;

$R^{16}$ is alkyl or aryl-$(CH_2)_m$—; and $R^{17}$ is hydrogen, alkyl, substituted alkyl, alkenyl, substituted alkenyl, cycloalkyl-$(CH_2)_m$—, aryl-$(CH_2)_m$—, substituted aryl-$(CH_2)_m$—, or heteroaryl-$(CH_2)_m$—.

$R^{18}$ is H, alkyl or alkenyl, and $R^{18}$ and $R^{17}$ may be taken together with the carbon and nitrogen to which they are attached to complete a saturated N-containing ring of 5 or 6 ring members.

$R^{19}$ is H or an alkyl, and in A(4), $R^{19}$ and X (which is $CH_2$) together with the carbons to which they are attached may form an aromatic ring of carbons (as in (15).

The starting compounds H-A(1) and H-A(2) are described in the literature or are obtained by modifications of known procedures. For example, the starting compounds of formula H-A(1) or H-A(2) wherein A(1) or A(2) is as defined in formulas A(5), A(13), A(16), A(21), where Y (where present) is $CH_2$ are disclosed by Thorsett et al., J. Med. Chem., 29, p. 251–260 (1988), Harris et al. in U.S. Pat. Nos. 4,587,050, 4,587,238, 4,629,787 and Yanagisawa et al. in U.S. Pat. No. 4,734,410.

The starting compounds of formula H-A(1) or H-A(2) wherein A(1) or A(2) is as defined in formulas A(3) and A(13) where Y is S(O)n are disclosed by Yanagisawa et al., J., Med. Chem., 30, p. 1984–1991 (1987) and 31, p. 422–428 (1988), Karanewsky in U.S. Pat. No. 4,460,579, Cheung et al. in U.S. Pat. No. 4,594,341, and Yanagisawa et al. in U.S. Pat. No. 4,699,905.

The starting compounds of formula H-A(1) or H-A(2) wherein A(1) or A(2) is as defined in formula A(5) are disclosed by Karanewsky in U.S. Pat. Nos. 4,460,579 and 4,711,884.

The starting compounds of formula H-A(1) or H-A(2) wherein A(1) or A(2) is as defined in formulas A(3) (Y is —$CH_2$—, and A(21) are disclosed by Watthey et al., J. Med. Chem., 28, p. 1511–1516 (1985) and Watthey in U.S. Pat. Nos. 4,410,520, 4,470,988, 4,473,575, 4,537,885 and 4,575, 503 and also by Parsons et al., Biochemical & Biophysical Research Comm., 117, p. 108–113 (1983) and in U.S. Pat. No. 4,873,235.

The starting compounds of formula H-A(1) or H-A(2) wherein A(1) or A(2) is as defined in formula A(3) and Y is S or O are disclosed by Slade et al., J. Med. Chem., 28, p. 1517–1521 (1985) and in U.S. Pat. No. 4,477,464 and Itoh et al., Chem. Pharm. Bull., 34, p. 1128–1147 (1986) and 34, p. 2078–2089 (1986) as well as Sugihara et al. in U.S. Pat. No. 4,548,932 (Y is O) and Katakami et al. in U.S. Pat. No. 4,539,150 (Y is S).

The starting compounds of formula H-A(1) or H-A(2) wherein A(1) or A(2) is as defined in formula A(16) can be prepared by reduction of the corresponding starting compounds wherein A(1) or A(2) is as defined in formula A(3).

The starting compounds of formula H-A(1) or H-A(2) wherein A(1) or A(2) is as defined in formula A(22) are disclosed by Flynn et al in U.S. Pat. No. 4,973,585.

The starting compounds of formula H-A(1) or H-A(2) wherein A(1) or A(2) is as defined in formula A(10) and Y is S, —SO, or —$SO^2$ are disclosed by Harris et al. and Patchett et al. in U.S. Pat. Nos. 4,415,496 and 4,617,301.

The starting compounds of formula H-A(1) or H-A(2) wherein A(1) or A(2) is as defined in formula A(10) and Y is $CH_2$, and is as defined in formula A(23) where $X^2$ is $CH_2$ is disclosed by Thorsett, Actual. Chim. Ther., 13, p. 257–268 (1986).

The starting compounds of formula H-A(1) or H-A(2) wherein A(1) or A(2) is as defined in formulas A(11) and A(19) and A(20) are disclosed by Attwood et al., Federation of European Biochemical Studies, 165, p. 201–206 (1984) and in U.S. Pat. No. 4,512,994 and Natoff et al., Drugs Of The Future, 12, p. 475–483 (1987).

The starting compounds of formula H-A(1) or H-A(2) wherein A(1) or A(2) is as defined in formula A(12) are disclosed by Huang et al. in U.S. Pat. No. 4,465,679.

The starting compounds of formula H-A(1) or H-A(2) wherein A(1) or A(2) is as defined in formula A(18) are disclosed by Bolos et al. in Tetrahedron, 48, p. 9567–9576 (1992).

The starting compounds of formula H-A(1) or H-A(2) wherein A(1) or A(2) is as defined in formulas A(4) and A(15) are disclosed in European Patent Application 0629627A2.

The starting compounds of formula H-A(1) or H-A(2) wherein A(1) or A(2) is as defined in formula A(9) are disclosed in U.S. application Ser. No. 100,408 (file HA611a).

The starting compounds of formula H-A(1) or H-A(2) wherein A(1) or A(2) is as defined in formulas A(7) and A(8)

are disclosed in European Patent Application 481,522 (Flynn et al) and European Patent Application 0534363A2 (Warshawsky et al).

The starting compounds of formula H-A(1) or H-A(2) wherein A(1) or A(2) is as defined in formula A(14) are disclosed in U.S. Pat. No. 5,525,723 issued Jun. 11, 1996.

The starting compounds of formula H-A(1) or H-A(2) wherein A(1) or A(2) is as defined in formula A(17) are disclosed in European Patent Application 0599444A1 (Barrish et al) and U.S. Pat. No. 5,552,397 issued Sep. 3, 1996.

The starting compound of formula H-A(1) or H-A(2) wherein A(1) or A(2) is as defined in formula A(24) is disclosed in U.S. Pat. No. 5,877,313.

The starting compound of formula H-A(1) or H-A(2) wherein A(1) or A(2) is as defined in formula A(23) is disclosed in WO94/10193 (Merrell Dow Pharmaceuticals).

The starting compound of formula H-A(1) or H-A(2) wherein A(1) or A(2) is as defined in formula A(25) is disclosed in WO95/01353 (Ciba Geigy).

In addition, in accordance with the present invention, a pharmaceutical composition is provided which includes a therapeutically effective amount of compound I and a pharmaceutically acceptable carrier therefor.

The pharmaceutical composition as defined above will be useful in the treatment of cardiovascular diseases such as hypertension and/or congestive heart failure.

Furthermore, in accordance with the present invention, a method is provided for treating a cardiovascular disease such as hypertension and/or congestive heart failure, as well as other diseases as set out hereinafter, which includes the step of administering to a mammalian species, including humans, dogs and cats, a therapeutically effective amount of a composition as defined above.

DETAILED DESCRIPTION OF THE INVENTION

The term "alkyl" or "lower alkyl" refers to straight or branched chain radicals having up to and including ten carbon atoms, preferably up to and including six carbon atoms, which may optionally include one, two, or three substituents including a hydroxy, amino, alkyl, cycloalkyl, aryl, halo, trifluoromethyl, cyano, —NH(lower alkyl), —N(lower alkyl)$_2$, lower alkoxy, lower alkylthio, carboxy or heteroaryl.

The term "alkenyl" refers to straight or branched chain radicals of 3 to 10 carbon atoms having one or two double bonds, preferably straight chain radicals of 3 to 5 carbons having one double bond, which may optionally be substituted with one, two or three substituents including alkyl, aryl, cycloalkyl, hydroxy, amino, halo, trifluoromethyl, cyano, —NH(lower alkyl), —N(lower alkyl)$_2$, lower alkoxy, lower alkylthio, carboxy or heteroaryl.

The terms "alkoxy" or "lower alkoxy" and "alkylthio" or "lower alkylthio" refer to such alkyl groups as defined above attached to an oxygen or sulfur.

The term "cycloalkyl" refers to saturated rings of 3 to 7 carbon atoms.

The term "halo" refers to chloro, bromo, fluoro, and iodo.

The term "aryl" refers to aromatic groups containing 6 to 10 carbons, preferably phenyl, 1-naphthyl, and 2-naphthyl, which may optionally contain one, two or three substituents selected from alkyl, alkoxy, alkylthio, halo, hydroxy, trifluoromethyl, —SO$_2$NH$_2$, amino, —NH(lower alkyl), or —N(lower alkyl)$_2$, di- and tri-substituted phenyl, 1-naphthyl, or 2-naphthyl, wherein said substituents are preferably selected from methyl, methoxy, methylthio, halo, hydroxy, and amino.

The term "heteroaryl" refers to unsaturated rings of 5 or 6 atoms containing one or two O and S atoms and/or one to four N atoms provided that the total number of hetero atoms in the ring is 4 or less, which may optionally be substituted with one, two or three substituents which include alkyl, aryl, cycloalkyl, alkoxy or halo. The heteroaryl ring is attached by way of an available carbon or nitrogen atom. Preferred heteroaryl groups include 2-, 3-, or 4-pyridyl, 4-imidazolyl, 4-thiazolyl, 2- and 3-thienyl, and 2- and 3-furyl. The term heteroaryl also includes bicyclic rings wherein the five or six membered ring containing O, S, and N atoms as defined above is fused to a benzene or pyridyl ring. Preferred bicyclic rings are 2- and 3-indolyl and 4- and 5-quinolinyl. The mono or bicyclic heteroaryl ring can also be additionally substituted at an available carbon atom by a lower alkyl, halo, hydroxy, benzyl, or cyclohexylmethyl. Also, if the mono or bicyclic ring has an available N-atom such N atom can also be substituted by an N-protecting group such as

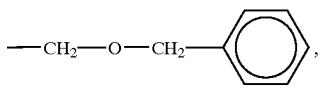

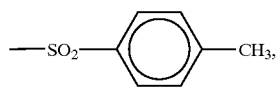

2,4-dinitrophenyl, lower alkyl, benzyl, or benzhydryl.

The term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker (CH$_2$)$_p$ (which is defined above), such as

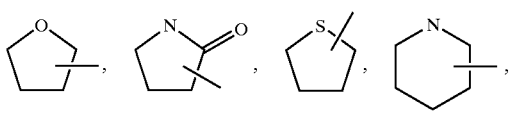

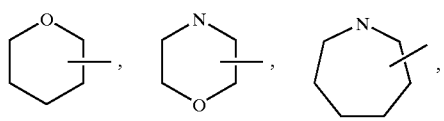

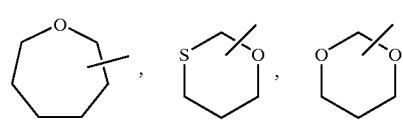

and the like. The above groups may include 1 to 4 substituents such as alkyl, halo, oxo and/or any of the substituents set out herein for alkyl. In addition, any of the above rings can be fused to a cycloalkyl, aryl, heteroaryl or cycloheteroalkyl ring.

The compounds of formula I of the invention may be prepared as outlined in Reaction Scheme I set out below (where x is 0 or 1).

(TFA, HCl) without effecting removal of $R^4$ when $R^4$ is OMe, OEt, or OBn. Additionally, when $R^{20}$ is OBn, OMe, or OEt, $R^{20}$ may be removed by treatment with base (aqueous NaOH) without effecting removal of $R^4$ when $R^4$ is O-t-butyl. Compound 4 may be reacted with a suitably O protected (e.g. PG1 is benzyl, p—methoxybenzyl,

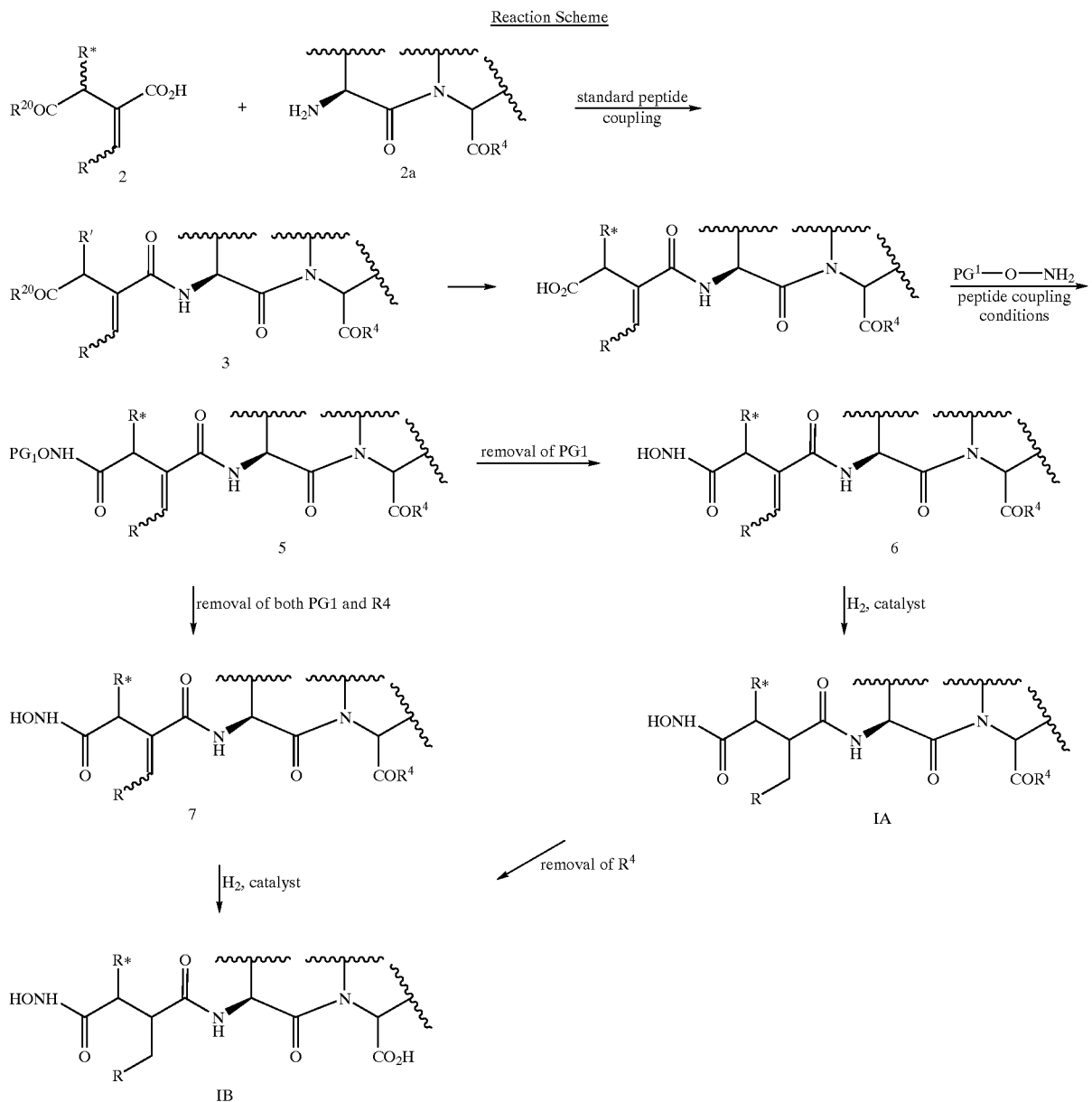

Reaction Scheme

As shown in the above Reaction Scheme, acid 2 may be coupled directly with amine H-A(1) or H-A(2) to give a mixture of diastereomers which may be separated.

Selective removal of $R^{20}$ in the presence of $COR^6$ may be effected by those knowledgeable in the field to give compound 4. For example, when $R^{20}$ is OBn or O-t-butyl, $R^{20}$ may be removed by treatment with TMSI without effecting removal of $R^4$ when $R^4$ is OMe or OEt. Additionally, when $R^{20}$ is O-t-butyl, $R^{20}$ may be removed by treatment with acid tetrahydropyranyl, trityl or benzhydryl) hydroxylamine to give the adduct 5. Selective removal of PG1 (such as acid treatment when PG1 is tetrahydropyranyl or trityl and $R^4$ is OMe or OEt affords 6 which may be converted to IA by hydrogenation of the double bond. Alternately, PG1 and $R^4$ can be removed either sequentially or simultaneously (in the case where PG1 and $R^4$ are Bn and OBn respectively) to give 7 which may be converted to IB by hydrogenation.

The compounds of formula I of the invention contain one or more asymmetric centers. Thus, these compounds can exist in diastereoisomeric forms or in mixtures thereof and all of such forms are within the scope of this invention. The above described processes can utilize racemates, enantiomers, or diastereomers as starting materials. When diastereomeric compounds are prepared, they can be separated by conventional chromatographic or fractional crystallization methods.

The compounds of formula I of the invention can be isolated in the form of a pharmaceutically acceptable salt. Suitable salts for this purpose are alkali metal salts such as sodium and potassium, alkaline earth metal salts such as calcium and magnesium, and salts derived from amino acids such as arginine, lysine, etc. These salts are obtained by reacting the acid form of the compound with an equivalent of base supplying the desired ion in a medium in which the salt precipitates or in aqueous medium and then lyophilizing.

The compounds of formula I of the invention are inhibitors of angiotensin converting enzyme and/or neutral endopeptidase. Thus, the compounds of formula I including their pharmaceutically acceptable salts are useful in the treatment of physiological conditions in which either angiotensin converting enzyme inhibitors or neutral endopeptidase inhibitors have been shown to be useful. Such conditions include cardiovascular diseases, particularly, hypertension, congestive heart failure, renal failure, angina, and hepatic cirrhosis, as well as analgesic activity.

Diuresis, natriuresis, and blood pressure reduction are produced in a mammalian host such as man by the administration of from about 1 mg. to about 100 mg. per kg. of body weight per day, preferably from about 1 mg. to about 50 mg. per kg. of body weight per day, of one or more of the compounds of formula I or a pharmaceutically acceptable salt thereof. The compounds of formula I are preferably administered orally, but parenteral routes such as subcutaneous, intramuscular, and intravenous can also be employed. The daily dose can be administered singly or can be divided into two to four doses administered throughout the day.

The ACE and/or NEP inhibitors of formula I can be administered in combination with human ANF 99–126. Such combination would contain the inhibitor of formula I at from about 1 to about 100 mg. per kg. of body weight and the human ANF 99–126 at from about 0.001 to about 0.1 mg. per kg. of body weight.

The ACE and/or NEP inhibitors of formula I can be administered in combination with other classes of pharmaceutically active compounds. For example, a calcium channel blocker, a potassium channel activator, a cholesterol reducing agent, etc.

The ACE and/or NEP inhibitors of formula I or a pharmaceutically acceptable salt thereof and other pharmaceutically acceptable ingredients can be formulated for the above described pharmaceutical uses. Suitable compositions for oral administration include tablets, capsules, and elixirs, and suitable compositions for parenteral administration include sterile solutions and suspensions. About 10 to 500 mg. of active ingredient is compounded with physiologically acceptable vehicle, carrier, excipient, binder, preservative, stabilizer, flavoring, etc., in a unit dose form as called for by accepted pharmaceutical practice.

Preferred compounds of the invention are those of formula I wherein $R^1$ is H, $R^*$ is H, R is alkyl or arylalkyl, and A is A(1), preferably where

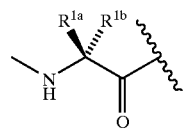

is preferably a non-proteinogenic amino acid portion wherein, $R^{1a}$ and $R^{1b}$ are each independently alkyl such as methyl or ethyl, or arylalkyl such as benzyl, or $R^{1a}$ and $R^{1b}$ together with the carbon to which they are attached form a 3–7 membered ring, preferably a 5-membered ring, or $R^{1a}$ and/or $R^{1b}$ is biphenylmethylene and the other may be H.

Also preferred are compounds where A is A(1), preferably where

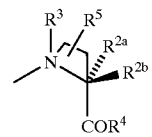

is a non-proteino-genic amino acid where $R^3$ is H, alkyl, such as methyl or ethyl, aryl such as phenyl, or arylalkyl, such as benzyl, $R^{2a}$ and $R^{2b}$ are independently selected from H, alkyl, aryl, arylalkyl (with at least one of $R^{2a}$ and $R^{2b}$ being other than H) or $R^{2a}$ and $R^{2b}$ together with the carbon to which they are attached form a 3–7 membered ring, preferably 5- or 6-membered ring.

Also preferred are compounds where A is A(2) wherein $R^4$ is OH.

The following Examples represent preferred embodiments of the present invention and may be prepared following procedures described above.

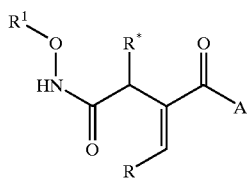
| Example No. | R¹ | R* | R | ‖ | A |
|---|---|---|---|---|---|
| 1 | H | H | Ph | ‖ | (bicyclic azepine-piperidine with NH, C=O, CO₂H) |
| 2 | H | H | Ph | | | (bicyclic azepine-piperidine with NH, C=O, CO₂H) |
| 3 | H | H | CH(CH₃)₂ | | | (thienyl-fused bicyclic with NH, C=O, CO₂H) |
| 4 | H | H | Ph | | | (thia-bicyclic with NH, C=O, CO₂H) |
| 5 | H | H | CH(CH₃)₂ | ‖ | (diaza-bicyclic with NH, C=O, CO₂H) |
| 6 | H | H | Ph | | | (azepanone with NH, propyl, Me, CO₂H) |
| 7 | H | H | Ph | | | (dimethyl azepanone with NHMe, CO₂H) |

-continued
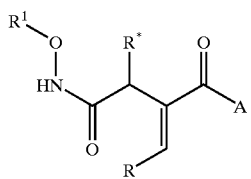
| Example No. | R¹ | R* | R | ‖ | A |
|---|---|---|---|---|---|
| 8 | H | H | Ph | ‖ | 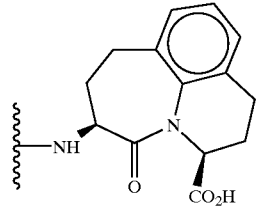 |
| 9 | H | H | CH(CH₃)₂ | | 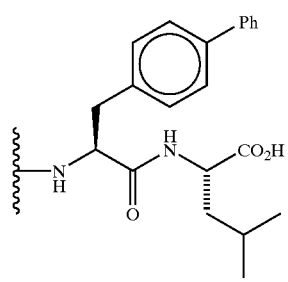 |
| 10 | H | H | CH(CH₃)₂ | | 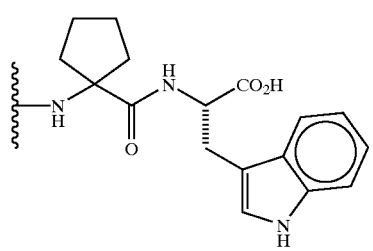 |
| 11 | H | H | CH(CH₃)₂ | | 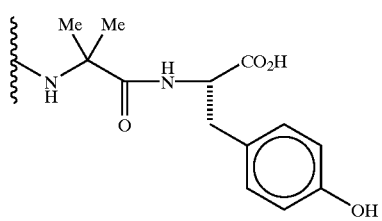 |
| 12 | H | H | Ph | ‖ | 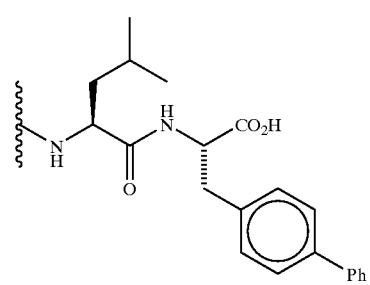 |

What is claimed is:

1. A method of treating hypertension and/or congestive heart failure, which comprises administering to a mammalian species a therapeutically effective amount of a compound of the formula

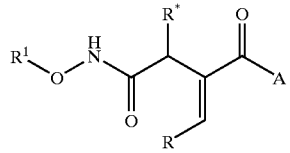

or a pharmaceutically acceptable salt thereof wherein in the moiety

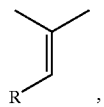

"||" denotes a single bond or a double bond, and the R group may be in the cis or trans configuration;

R and R* are the same or different and are independently selected from H, alkyl, alkenyl, aryl-$(CH_2)_p$—, heteroaryl-$(CH_2)_p$—, or cycloheteroalkyl-$(CH_2)_p$—;

$R^1$ is H or —$COR^2$ where $R^2$ is alkyl, aryl-$(CH_2)_p$—, cycloheteroalkyl-$(CH_2)_p$—, heteroaryl-$(CH_2)_p$—, alkoxy or cycloalkyl-$(CH_2)_p$—;

p is 0 or an integer from 1 to 8; and

A is

$R^4$ is OH, Oalkyl, O—$(CH_2)_p$-heteroaryl,

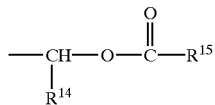

—O—$(CH_2)_p$-aryl or

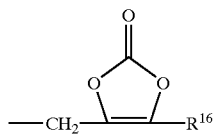

or $NR_1(R_2)$ where $R_1$ and $R_2$ are independently H, alkyl, aryl, aryl-$(CH_2)_p$ or heteroaryl;

$R^{14}$ is hydrogen, alkyl, cycloalkyl, or phenyl;

$R^{15}$ is hydrogen, alkyl, alkoxy or phenyl;

$R^{16}$ is alkyl or aryl-$(CH_2)_m$—; and $R^7$ is selected from hydrogen, alkyl, alkenyl, cycloalkyl-$(CH_2)_m$—, aryl-$(CH_2)_m$—, and heteroaryl-$(CH_2)_m$—, where m is 0 to 6;

$R^{11}$ and $R^{12}$ are independently selected from hydrogen, alkyl, alkenyl, cycloalkyl-$(CH_2)_p$—, aryl-$(CH_2)_p$—, and heteroaryl-$(CH_2)_p$—, or $R^{11}$ and $R^{12}$ taken together with the carbon to which they are attached complete a saturated cycloalkyl ring of 3 to 7 carbons, or $R^{11}$ and $R^{12}$ taken together with the carbon to which they are attached complete a keto substituent, with the proviso that at least one or $R^{11}$ and $R^{12}$ is other than H, wherein the term "heteroaryl" refers to an unsaturated ring of 5 or 6 atoms containing one or two O and S atoms and/or 1 to 4 N atoms provided that the total number of hetero atoms in the ring is 4 or less, which may optionally be substituted with 1, 2 or 3 substituents, wherein the above 5 or 6-membered ring is optionally fused to a benzene or pyridyl ring to form a bicyclic ring, which mono or bicyclic ring can also be additionally substituted at an available carbon atom, and if the mono or bicyclic ring has an available N-atom such N atom can also be substituted by an N-protecting group;

the term "cycloheteroalkyl" refers to a 5-, 6 - or 7-membered saturated or partially unsaturated ring which includes 1 to 2 hetero atoms which are nitrogen, oxygen and/or sulfur, linked through a carbon atom or a heteroatom, and which may include 1 to 4 substituents, and the 5-, 6-, or 7-membered ring can be fused to a cycloalkyl, aryl, heteroaryl or cycloheteroalkyl ring; and the term "cycloalkyl" refers to saturated rings of 3 to 7 carbons.

2. The method as defined in claim 1 where in the compound administered, $R^1$ is H, R is alkyl or arylalkyl, $R^4$ is OH and $R^{11}$ and $R^{12}$ are each methyl.

3. A compound having the structure

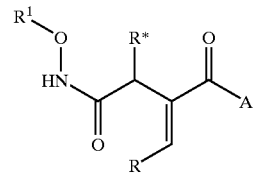

where $R^1$ is H, R* is H, R is Ph and A is

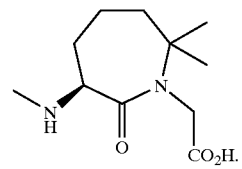

4. A pharmaceutical composition comprising a therapeutically effective amount of a compound as defined in claim 3 and a pharmaceutically acceptable carrier therefor.

* * * * *